(12) United States Patent
Pelicci et al.

(10) Patent No.: US 7,858,329 B2
(45) Date of Patent: Dec. 28, 2010

(54) ANTIBODY TOOLS FOR THE DIAGNOSTIC USE IN THE MEDICAL THERAPY WITH INHIBITORS OF HISTONE DEACETYLASES

(75) Inventors: Giuseppe Pier Pelicci, Opera (IT); Saverio Minucci, Opera (IT); Daniele Piccini, Locate de Triulzi (IT); Marco Maccarana, Seriate (IT); Simona Ronzoni, Mariano Comense (IT); Beatriz Liliana Areces, Milan (IT); Mario Faretta, Corsico (IT)

(73) Assignee: TopoTarget Germany AG, Frankfurt am Main (DE)

( * ) Notice: Subject to any disclaimer, the term of this patent is extended or adjusted under 35 U.S.C. 154(b) by 966 days.

(21) Appl. No.: 10/529,792

(22) PCT Filed: Sep. 30, 2003

(86) PCT No.: PCT/EP03/10842

§ 371 (c)(1),
(2), (4) Date: Nov. 10, 2005

(87) PCT Pub. No.: WO2004/029622

PCT Pub. Date: Apr. 8, 2004

(65) Prior Publication Data

US 2006/0257948 A1 Nov. 16, 2006

(30) Foreign Application Priority Data

Sep. 30, 2002 (EP) .................................. 02021984

(51) Int. Cl.
C07K 16/30 (2006.01)
G01N 33/574 (2006.01)
C12N 5/06 (2006.01)

(52) U.S. Cl. .................... 435/7.23; 435/338; 530/388.8
(58) Field of Classification Search ................ 435/7.23, 435/338; 530/388.8
See application file for complete search history.

(56) References Cited

U.S. PATENT DOCUMENTS

| 7,256,013 B2 | 8/2007 | Tamai et al. |
| 7,276,234 B1 | 10/2007 | Takahama et al. |
| 7,632,507 B2 | 12/2009 | Nakajima et al. |
| 2004/0152871 A1 | 8/2004 | Nakajima et al. |
| 2004/0198959 A1* | 10/2004 | Komatsu et al. .......... 530/388.1 |

FOREIGN PATENT DOCUMENTS

| EP | 1050581 A1 * | 8/2000 |
| EP | 1 050 581 | 11/2000 |
| EP | 02021228.8 * | 9/2002 |
| JP | 10-298101 | 11/1998 |
| JP | 10-298101 A2 | 11/1998 |
| JP | 2001-501190 | 1/2001 |
| JP | 2001501190 T2 | 1/2001 |
| WO | 9811920 A2 | 3/1998 |
| WO | WO 98-11919 | 3/1998 |
| WO | 9936532 A1 | 7/1999 |
| WO | WO 99/36532 | 11/2000 |
| WO | 02052007 A1 | 7/2002 |
| WO | WO 02/052007 | 7/2002 |
| WO | WO 02/074962 | 9/2002 |

OTHER PUBLICATIONS

Hoffmann et al. (Bioconjug. Chem. Jan.-Feb. 2001;12(1):51-5) (Abstract).*
Merriam-Webster on-line definition of "derived".*
Ono et al. (J. Exp. Clin. Can. Res. 21(3):377-382 (Sep. 2002); Abstract).*
Marquard et al. (APMIS 116:382-392 (2008)).*
Butler L M et al "Inhibition of Transformed Cell Growth and Induction of Cellular Differentiation by Pyroxamide, an Inhibitor of Histone Deacetylase." Clinical Cancer Research: An Official Journal of the American Association for Cancer Research. US Apr. 2001, vol. 7, No. 4, pp. 962-970.
Marks Paul A et al: "Histone Deacetylases and Cancer: Causes and Therapies." Nature Reviews Cancer, vol. 1, No. 3, Dec. 20, 2001, pp. 194-202.
White D A et al: "Preparation of Site-Specific Antibodies to Acetylated Histones" Methods: A Companion to Methods in Enzymology, Academic Press Inc., NY, vol. 19, 1999, pp. 417-424.
Bodey et al., "Human Cancer Detection and Immunotherapy with Conjugated and Non-Conjugated Monoclonal Antibodies", AntiCancer Research, vol. 16 (1996), pp. 661-674.
Butler et al., "Inhibition of Transformed Cell Growth and Induction of Cellular Differentiation by Pyroxamide, an Inhibitor of Histone Deacetylase", Clinical Cancer Research, vol. 7, pp. 962-970, Apr. 2001.
Marks et al., "Histone Deacetylases and Cancer: Causes and Therapies", Nature Reviews, vol. 1, pp. 194-202, Dec. 2001.
White et al., "Preparation of Site-Specific Antibodies to Acotylated Histones", Methods, vol. 19, pp. 417-424, 1999.
Aherne et al., "Assays for the identification and evaluation of histone acetyltransferase inhibitors", Methods, vol. 28, pp. 245-253, 2002.

* cited by examiner

*Primary Examiner*—Lynn Bristol
(74) *Attorney, Agent, or Firm*—Millen, White, Zelano, Branigan, P.C.

(57) ABSTRACT

The invention relates to a method for determining whether a treatment of a disorder with an HDAC inhibitor is to be started/continued or not comprising determining the level of histone acetylation in the sample by use of an antibody capable of binding to acetylated histone, and classifying the disorder as to be treated with an HDAC inhibitor when the level of histone acetylation is significantly lower than that of a reference sample. The invention further relates to the diagnostic and prognostic use of specific antibodies and cell lines producing them.

12 Claims, 12 Drawing Sheets

Figure 1

| ELISA analysis (average from triplicates): | OD values | |
|---|---|---|
| | T52 | T25 |
| Histone H4 | 2 µg/ml | 2 µg/ml |
| 8 mono-Ac (SEQ ID NO:4) | 683 | 1367 |
| 12 mono-Ac (SEQ ID NO:5) | 940 | 552 |
| 16 mono-Ac (SEQ ID NO:6) | 101 | 0 |
| 5, 12 di-Ac (SEQ ID NO:7) | 822 | 585 |
| 8, 16 di-Ac (SEQ ID NO:8) | 884 | 1296 |
| 8, 12, 16 tri-Ac (SEQ ID NO:9) | 1485 | 1436 |
| 5, 8, 12, 16 tetra-Ac (SEQ ID NO:1) | 1408 | 1443 |
| non-acetylated (SEQ ID NO:2) | 0 | 0 |
| Unrelated peptides | | |
| tri-Ac (SEQ ID NO:10) | 935 | 0 |
| mono-Ac (SEQ ID NO:11) | 742 | 0 |

Figure 2

| ELISA analysis at different concentrations of Antibody: | OD values | |
|---|---|---|
| | T52 | T25 |
| | 1/10 µg/ml | 1/5 µg/ml |
| 8 mono-Ac (SEQ ID NO:4) | 398/914 | 1460/1446 |
| 12 mono-Ac (SEQ ID NO:5) | 705/1070 | 522/933 |
| 16 mono-Ac (SEQ ID NO:6) | 40/200 | 002/55 |
| 5, 12 di-Ac (SEQ ID NO:7) | 624/986 | 514/868 |
| 8, 16 di-Ac (SEQ ID NO:8) | 565/1097 | 1255/1260 |
| 8, 12, 16 tri-Ac (SEQ ID NO:9) | 1288/1506 | 1372/1276 |
| 5, 8, 12, 16 tetra-Ac (SEQ ID NO:1) | 1183/1439 | 1383/1324 |
| not-Ac (SEQ ID NO:2) | 0/0 | 007/48 |

Breast Cancer

Breast Cancer

Normal Breast

ANTIBODY TOOLS FOR THE DIAGNOSTIC USE IN THE MEDICAL THERAPY WITH INHIBITORS OF HISTONE DEACETYLASES

This application is a National Stage entry under 35 USC §371 of PCT/EP03/10842, filed Sep. 30, 2003, and claims priority to EP02021984.6, filed Sep. 30, 2002.

The present invention relates to the use of specific antibody tools for the diagnostic and prognostic use in the treatment of tumor patients with inhibitors of enzymes having histone deacetylase activity. The invention also relates to the production of diagnostic and prognostic tool systems based on these antibodies.

Gene Regulation and Histone Acetylation

Local remodeling of chromatin is a key step in the transcriptional activation of genes. Dynamic changes in the nucleosomal packaging of DNA must occur to allow transcriptional proteins to contact with the DNA template. One of the most important mechanisms influencing chromatin remodeling and gene transcription are the posttranslational modification of histones and other cellular proteins by acetylation and subsequent changes in chromatin structure (Davie, 1998, Curr Opin Genet Dev 8, 173-8; Kouzarides, 1999, Curr Opin Genet Dev 9, 40-8; Strahl and Allis, 2000, Nature 403, 41-4). In the case of histone hyperacetylation, changes in electrostatic attraction for DNA and steric hindrance introduced by the hydrophobic acetyl group leads to destabilisation of the interaction of histones with DNA. As a result, acetylation of histones disrupts nucleosomes and allows the DNA to become accessible to the transcriptional machinery. Removal of the acetyl groups allows the histones to bind more tightly to DNA and to adjacent nucleosomes and thus to maintain a transcriptionally repressed chromatin structure. Acetylation is mediated by a series of enzymes with histone acetyltransferase (HAT) activity. Conversely, acetyl groups are removed by specific histone deacetylase (HDAC) enzymes. Disruption of these mechanisms gives rise to transcriptional misregulation and may lead to tumorigenic transformation.

Additionally, other molecules such as transcription factors alter their activity and stability depending on their acetylation status. E.g. PML-RAR, the fusion protein associated with acute promyelocytic leukemia (APL) inhibits p53 through mediating deacetylation and degradation of p53, thus allowing APL blasts to evade p53 dependent cancer surveillance pathways. Expression of PML-RAR in hematopoietic precursors results in repression of p53 mediated transcriptional activation, and protection from p53-dependent apoptosis triggered by genotoxic stresses (X-rays, oxidative stress). However, the function of p53 is reinstalled in the presence of HDAC inhibitors implicating active recruitment of HDAC to p53 by PML-RAR as the mechanism underlying p53 inhibition (Insinga et al. 2002, manuscript submitted). Therefore, factor acetylation plays a crucial role in the anti-tumor activity of HDAC inhibitors.

Nuclear hormone receptors are ligand-dependent transcription factors that control development and homeostasis through both positive and negative control of gene expression. Defects in these regulatory processes underlie the causes of many diseases and play an important role in the development of cancer. Many nuclear receptors, including T3R, RAR and PPAR, can interact with the corepressors N-CoR and SMRT in the absence of ligand and thereby inhibit transcription. Furthermore, N-CoR has also been reported to interact with antagonist-occupied progesterone and estrogen receptors. N-CoR and SMRT have been shown to exist in large protein complexes, which also contain mSin3 proteins and histone deacetylases (Pazin and Kadonaga, 1997; Cell 89, 325-8). Thus, the ligand-induced switch of nuclear receptors from repression to activation reflects the exchange of corepressor and coactivator complexes with antagonistic enzymatic activities.

The N-CoR corepressor complex not only mediates repression by nuclear receptors, but also interacts with additional transcription factors including Mad-1, BCL-6 and ETO. Many of these proteins play key roles in disorders of cell proliferation and differentiation (Pazin and Kadonaga, 1997, Cell 89, 325-8; Huynh and Bardwell, 1998, Oncogene 17, 2473-84; Wang, J. et al., 1998, Proc Natl Acad Sci USA 95, 10860-5). T3R for example was originally identified on the basis of its homology with the viral oncogene v-erbA, which in contrast to the wild type receptor does not bind ligand and functions as a constitutive repressor of transcription. Furthermore, mutations in RARs have been associated with a number of human cancers, particularly acute promyelocytic leukemia (APL) and hepatocellular carcinoma. In APL patients RAR fusion proteins resulting from chromosomal translocations involve either the promyelocytic leukemia protein (PML) or the promyelocytic zinc finger protein (PLZF). Although both fusion proteins can interact with components of the corepressor complex, the addition of retinoic acid dismisses the corepressor complex from PML-RAR, whereas PLZF-RAR interacts constitutively. These findings provide an explanation why PML-RAR APL patients achieve complete remission following retinoic acid treatment whereas PLZF-RAR APL patients respond very poorly (Grignani et al., 1998, Nature 391, 815-8; Guidez et al., 1998, Blood 91, 2634-42; He et al., 1998, Nat Genet 18, 126-35; Lin et al., 1998, Nature 391, 811-4). Furthermore, a PML-RAR patient who had experienced multiple relapses after treatment with retinoic acid has recently been treated with the HDAC inhibitor phenylbutyrate, resulting in complete remission of the leukemia (Warrell et al., 1998, J. Natl. Cancer Inst. 90, 1621-1625).

Inhibition of Histone Deacetylases

By now, a clinical phase II trial with the closely related butyric acid derivative Pivanex (Titan Pharmaceuticals) as a monotherapy has been completed demonstrating activity in stage III/IV non-small cell lung cancer (Keer et al., 2002, ASCO, Abstract No. 1253). More HDAC inhibitors have been identified, with NVP-LAQ824 (Novartis) and SAHA (Aton Pharma Inc.) being members of the structural class of hydroxamic acids tested in phase I clinical trials (Marks et al., 2001, Nature Reviews Cancer 1, 194-202). Another class comprises cyclic tetrapeptides, such as depsipeptide (FR901228—Fujisawa) used successfully in a phase II trial for the treatment of T-cell lymphomas (Piekarz et al., 2001, Blood 98, 2865-8). Furthermore, MS-27-275 (Mitsui Pharmaceuticals), a compound related to the class of benzamides, is now being tested in a phase I trial patients with hematological malignancies.

The recruitment of histone acetyltransferases (HATs) and histone deacetylases (HDACs) is considered as a key element in the dynamic regulation of many genes playing important roles in cellular proliferation and differentiation. Hyperacetylation of the N-terminal tails of histones H3 and H4 correlates with gene activation whereas deacetylation can mediate transcriptional repression. Consequently, many diseases have been linked to changes in gene expression caused by mutations affecting transcription factors. Aberrant repression by leukemia fusion proteins such as PML-RAR, PLZF-RAR, AML-ETO and Stat5-RAR serves as a prototypical example in this regard. In all of these cases, chromosomal translocations convert transcriptional activators into repressors, which constitutively repress target genes important for hematopoietic differentiation via recruitment of HDACs. It is plausible that similar events could also contribute to pathogenesis in many other types of cancer.

Mammalian histone deacetylases can be divided into three subclasses (Gray and Ekström, 2001, Exp Cell Res, Jan 15; 262(2):75-83). HDACs 1, 2, 3, and 8 which are homologues of the yeast RPD3 protein constitute class I. HDACs 4, 5, 6, 7, 9, and 10 are related to the yeast Hda 1 protein and form class II. Recently, several mammalian homologues of the yeast Sir2 protein have been identified forming a third class of deacetylases which are NAD dependent. All of these HDACs appear to exist in the cell as subunits of a plethora of multi-protein complexes. In particular, class I and II HDACs have been shown to interact with transcriptional corepressors mSin3, N-CoR and SMRT which serve as bridging factors required for the recruitment of HDACs to transcription factors.

Molecular Markers in Therapy of Human Cancer

The discovery of new molecular markers for diagnosis and staging of human cancer is still an ongoing task and is essential for choosing the right therapeutic strategy. In the case of breast cancer, molecular markers such as the level of HER2/neu, p53, BCL-2 and estrogen/progesterone receptor expression have been clearly shown to correlate with disease status and progression. Thus, a newly approved kit measuring HER2 concentration in the serum of patients with metastatic breast cancer can now be used for follow-up and monitoring of these patients. Recently, several large studies have shown that HER2 serum concentration is related to severity of disease, and—more importantly—in patients who respond to therapy, HER2 concentration decreases, irrespective of the type of therapy. This example demonstrates the value of diagnostic and prognostic markers in cancer therapy.

Medical Need for New Diagnostic and Prognostic Tools Related to HDAC Inhibitors

The clinical benefits of HDAC inhibition and their implications for cancer therapy are currently being investigated in several locations. Although results from initial studies indicate that HDAC inhibitors may be beneficial in the treatment of acute myeloid leukemia, T-cell lymphoma, and lung cancer, it is highly likely that also other cancer entities may be treated effectively. As yet, many of the currently developed HDAC inhibitors under investigation display side effects demanding further development of new generation of HDAC inhibitors. It is therefore essential to identify a characteristic profile for successful candidates as HDAC inhibitors. This may have dramatic consequences for saving cost and time in the development of new compounds. The second major task will then be to identify at an early stage the right patients who will benefit from a therapy with these HDAC inhibitors and to monitor these patients during therapy. Both questions are addressed in the present patent application.

The present invention aims at providing diagnostic and/or prognostic tools for the development and use of HDAC inhibitors. Therefore, one aspect of the present invention is the use of specific antibody tools to investigate the acetylation status of histones, in particular but not limited to histone H4.

The invention relates to a method for determining whether a treatment of a disorder with an HDAC inhibitor is to be started/continued or not comprising (a) contacting a sample derived from tissue affected by the disorder with an antibody capable of binding to acetylated histone but not to deacetylated histone;

(b) determining the level of histone acetylation in the sample; and (c) classifying the disorder as to be treated with an HDAC inhibitor when the level of histone acetylation is significantly lower than that in a reference sample.

The term "sample" as used herein designates a composition which is derived from tissue of an individual. A tissue affected by a disorder is a tissue which differs from the corresponding tissue from a healthy individual. The difference may be a difference in morphology, histology, gene expression, response to treatment, protein composition etc. The tissue affected by the disorder may be tumor tissue in the case of cancer diseases, such as but not limited to tissues of skin cancer, melanoma, estrogen receptor-dependent and independent breast cancer, ovarian cancer, testosteron receptor-dependent and independent prostate cancer, renal cancer, colon and colorectal cancer, pancreatic cancer, bladder cancer, esophageal cancer, stomach cancer, genitourinary cancer, gastrointestinal cancer, uterine cancer, astrocytomas, gliomas, basal cancer and squameous cell carcinoma, sarcomas as Kaposi's sarcoma and osteosarcoma, head and neck cancer, small cell and non-small cell lung carcinoma, leukemia, lymphomas and other blood cell cancers. The sample may be tissue material obtained through biopsy e.g. from a solid tumor of an individual. The tissue affected by the disorder includes cell lines which have been established from tumor tissue and transformed cell lines. Preferably, the sample is a composition which has been processed to be in a condition suitable for the method of determining the level of histone acetylation (step (b)). The processing may include homogenization, extraction, fixation, washing and/or permeabilization. The type of processing largely depends on the technique which is used for determining the level of histone acetylation (step (b)). A prerequisite is that the sample contains histone protein(s) from the tissue. The method of the invention comprises only steps which are carried out in vitro. Therefore, the step of obtaining the tissue material from the human or animal body is not encompassed by the present invention.

In a first embodiment, the reference sample is a sample which has been derived from tissue of a healthy individual. The tissue from which this reference sample has been derived corresponds to the tissue affected by the disorder. For example, if the tissue affected by the disorder is tumor tissue from a breast cancer patient the tissue from which the reference sample has been derived is breast tissue from a healthy individual. The reference sample is usually processed in the same way as the sample derived from tissue affected by the disorder (steps (a) and (b)). If the histone acetylation level in a certain tissue of a healthy individual is already known it is only required to determine the level of histone acetylation in the sample affected by the disorder. For example, it may be envisaged that data on histone acetylation in a large number of tissues from healthy individuals are collected. Once these data have been collected, one only has to examine the sample derived from tissue affected by a disorder to determine whether a treatment with an HDAC inhibitor is to be started/continued or not.

In a second embodiment, the reference sample is a further sample derived from tissue affected by the disorder. In this embodiment, the reference sample or the cells from which it has been derived have been contacted with an HDAC inhibitor (HDACi). For example, the sample may be derived from cancer tissue of a patient. Then the patient is treated with an HDAC inhibitor, and the reference sample is obtained from the same patient upon HDACi treatment. The reference sample may also be derived from cancer tissue of another patient suffering from the same disease who has been treated with HDACi. The sample may also be derived from cell culture cells, and the reference sample from a parallel culture of the same type of cells which have been treated with HDACi. The reference sample is subsequently processed in the same way as the first sample derived from tissue affected by the disorder (steps (a) and (b)). Usually, parallel samples are prepared which are processed identically except for the HDACi treatment. HDAC inhibitors which may be used include Trichostatin A, valproic acid and derivatives thereof, and other inhibitors known in the art. An increased level of histone acetylation in the reference sample which has been treated with HDAC inhibitor (+HDACi) compared to the sample which has not been treated with HDAC inhibitor (−HDACi) indicates that the cells of the tissue affected by the disorder respond to HDAC inhibitor treatment. The disorder may thus be classified as to be treated with an HDAC inhibitor.

In a third embodiment, the above-mentioned first and second embodiments are combined, i.e. one compares the histone acetylation level in the sample derived from tissue affected by the disorder with that of at least two reference samples. The first reference sample is from a healthy individual whereas the second reference sample is derived from tissue affected by the disorder and has been contacted with HDAC inhibitor (see supra).

The monitoring of the efficacy of HDACi treatment in patients is encompassed by the present invention. Various reference samples may be taken at different time points from a patient who is continuously treated with HDACi. The histone acetylation level is determined according to steps (a) and (b). When during HDACi treatment the level of histone acetylation remains significantly higher than that prior to HDACi treatment (the time point when the sample has been taken) the treatment may be considered as being efficient and be continued. When the level of histone acetylation in spite of continued HDACi treatment remains low or after an initial increase decreases again and approaches the level in the sample, the treatment may be inefficient.

The term "significantly lower" indicates that the difference in acetylation level is statistically significant. Preferably, the disorder is classified as to be treated with an HDAC inhibitor when the histone acetylation level is at least 25% lower than that in the reference sample, preferably at least 50%, more preferably at least 75%.

As used herein, the term "antibody" designates an immunoglobulin or a derivative thereof having the same binding specificity. The antibody according to the invention may be a monoclonal antibody or an antibody derived from or comprised in a polyclonal antiserum, monoclonal antibodies are preferred. The term "antibody", as used herein, further comprises derivatives such as Fab, $F(ab')_2$, Fv or scFv fragments: see, for example Harlow and Lane, "Antibodies, A Laboratory Manual" CSH Press 1988, Cold Spring Harbor N.Y.

The antibody or the derivative thereof may be of natural origin or may be (semi)synthetically produced. Such synthetic products also comprises non-proteinaceous or semi-proteinaceous material that has the same or essentially the same binding specificity as the antibody of the invention. Such products may, for example be obtained by peptidomimetics.

The antibody to be used according to the invention is capable of binding to an acetylated histone, preferably to acetylated histone H4, more preferably to acetylated human histone H4. The acetylation of the histone may be at any lysine residue of the amino acid sequence, preferably the acetylation is at lysines at position 6, 9, 13 and/or position 17 of human histone H4 (see for reference amino acid sequence of human histone H4 in Swiss Prot P02304 and therein with the first Methionine being position 1). The antibody does not bind to deacetylated histone, preferably deacetylated histone H4, more preferably deacetylated human histone H4.

In one embodiment, the antibody binds to acetylated histones, but may also bind to acetylated lysine in another context. Such antibody may crossreact with acetylated non-histone proteins, such as the tumor suppressor protein p53. An antibody according to this embodiment may bind to peptides having sequences as shown in SEQ ID NO:1, SEQ ID NO:10 and SEQ ID NO:11 but not to a peptide having the sequence as shown in SEQ ID NO:2. It may additionally be capable of binding to peptides having sequences as shown in SEQ ID NO:4, SEQ ID NO:5 and SEQ ID NO:6. A preferred antibody which can be used is the antibody termed T52 which is obtainable from the cell line termed G2M-T52-ac deposited at DSMZ (Deutsche Sammlung von Mikroorganismen und Zellkulturen, Mascheroder Weg 1b, D-38124 Braunschweig, Germany; German Collection of Microorganisms and Cell Cultures).

In another embodiment, the antibody binds to acetylated histones but not to acetylated lysine in another context. Such antibody does not crossreact with acetylated non-histone proteins. An antibody according to this embodiment may bind to a peptide having the sequence as shown in SEQ ID NO:1 but not to peptides having the sequences as shown in SEQ ID NO:2, SEQ ID NO:10 and SEQ ID NO:11. It may additionally bind to peptides having the sequences as shown in SEQ ID NO:4 and SEQ ID NO:5 but not to a peptide having the sequence as shown in SEQ ID NO:6. A preferred antibody used according to the invention is capable of binding to a peptide having the sequence as shown in SEQ ID NO:4 but not to anyone of the peptides having the sequences as shown in SEQ ID NO:2, SEQ ID NO:6, SEQ ID NO:10 and SEQ ID NO:11. The most preferred antibody is the antibody termed T25 which is obtainable from the cell line termed G2M-T25-H4ac deposited at DSMZ.

The method of the invention allows the determination whether a treatment of a disorder with an HDAC inhibitor is to be started. An important aspect of the method of the present invention is therefore the use of these antibody tools to identify patients and tumor entities that respond to a therapy with the HDAC inhibitors.

The method also allows the determination whether a treatment of a disorder with an HDAC inhibitor is to be continued. Thus, these antibody tools can be used to monitor efficacy of HDAC inhibitor treatment in patients.

This prognostic and diagnostic monitoring is suitable for disorders or diseases in which the induction of hyperacetylation of histones has a beneficial effect resulting in differentiation and/or apoptosis of a patient's tumor cells and thus causing a clinical improvement of the patient's condition. Examples of such diseases include but are not limited to, skin cancer, melanoma, estrogen receptor-dependent and independent breast cancer, ovarian cancer, testosteron receptor-dependent and independent prostate cancer, renal cancer, colon and colorectal cancer, pancreatic cancer, bladder cancer, esophageal cancer, stomach cancer, genitourinary cancer, gastrointestinal cancer, uterine cancer, astrocytomas, gliomas, basal cancer and squameous cell carcinoma, sarcomas as Kaposi's sarcoma and osteosarcoma, head and neck cancer, small cell and non-small cell lung carcinoma, leukemia, lymphomas and other blood cell cancers.

Yet another aspect of the invention is the use of these antibody tools in disorders or diseases that show aberrant recruitment of histone deacetylase activity such as thyroid resistance syndrome, or other conditions associated with abnormal gene expression, such as inflammatory disorders, diabetes, thalassemia, cirrhosis, protozoal infection, or the like and all types of autoimmune diseases, in particular rheumatoid arthritis, rheumatoid spondylitis, all forms of rheumatism, osteoarthritis, gouty arthritis, multiple sclerosis, insulin dependent diabetes mellitus and non-insulin dependent diabetes, asthma, rhinitis, uveithis, lupus erythematoidis, ulcerative colitis, Morbus Crohn, inflammatory bowel disease, as well as other chronic inflammations, chronic diarrhea.

Furthermore, the invention concerns the diagnostic and prognostic use of the above mentioned antibody tools in other proliferative disorders such as psoriasis, fibrosis and other dermatological disorders. The terms "proliferative disease", "proliferative disorder" and "cell proliferation", are used interchangeably herein and relate to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including malignant neoplasms and tumors, cancers, leukemias, psoriasis, bone disease, fibroproliferative disorders (e.g. of connective tissues), and atherosclerosis. Any type of cell may be treated, including but not limited to, lung, colon, breast, ovarian, prostate, liver, pancreas, brain, and skin and any treatment of disorders involving T-cells such as aplastic anemia and DiGeorge syndrome, Graves' disease.

In one embodiment, the determination whether a disorder is to be treated with an HDAC inhibitor means the determination whether a given disorder generally is to be treated with an HDAC inhibitor. In another embodiment, the determination whether a disorder is to be treated with an HDAC inhibitor means the determination whether a given patient is to be treated with an HDAC inhibitor.

The level of histone acetylation can be determined by a variety of methods. Western Blotting may be used which is a method known in the art. The tissue material may be treated with denaturing and/or reducing agents to obtain the sample. The sample may be loaded on a polyacrylamide gel to separate the proteins followed by transfer to a membrane or directly be spotted on a solid phase. The antibody is then contacted with the sample. After one or more washing steps the bound antibody is detected using techniques which are known in the art. Gel electorphoresis of proteins and Western Blotting is described in Golemis, "Protein-Protein Interactions: A Laboratory Manual", CSH Press 2002, Cold Spring Harbor N.Y.

Immunohistochemistry may be used after fixation and permeabilisation of tissue material, e.g. slices of solid tumors. The antibody is then incubated with the sample, and following one or more washing steps the bound antibody is detected. The techniques are outlined in Harlow and Lane, "Antibodies, A Laboratory Manual" CSH Press 1988, Cold Spring Harbor N.Y.

In a preferred embodiment, the level of histone acetylation is determined by way of an ELISA. A variety of formats of the ELISA can be envisaged. In one format, the antibody is immobilized on a solid phase such as a microtiter plate, followed by blocking of unspecific binding sites and incubation with the sample. In another format, the sample is first contacted with the solid phase to immobilize the histones contained in the sample. After blocking and optionally washing, the antibody is contacted with the immobilized sample. ELISA techniques are described in Harlow and Lane, "Antibodies, A Laboratory Manual" CSH Press 1988, Cold Spring Harbor N.Y.

Most preferably, the level of histone acetylation is determined by flow cytometry. Cells obtained from the tissue affected by the disorder, e.g. blood cells or cells from bone marrow, are fixed and permeabilized to allow the antibody to reach nuclear proteins. After optional washing and blocking steps the antibody is contacted with the cells. Flow cytometry is then performed in accordance with procedures known in the art in order to determine cells having antibody bound to their histones. Various flow cytometry methods are described in Robinson "Current Protocols in Cytometry" John Wiley & Sons Inc., New York. A method of quantitatively determining the level of histone acetylation is shown in Example 3.

Specific Diagnostic and Prognostic Detection of Histone Acetylation

As mentioned above detection of cellular histone acetylation levels can provide an important tool in monitoring the cellular response to specific anticancer treatments. For example, through detection of histone acetylation levels clinical treatment with HDACi (HDAC inhibitor) may be optimized, such as evaluating the dosages sufficient to achieve a biological response, without reaching toxic levels. Although Western blot analysis can be used in some cases, it requires preparation of cellular extracts, and does not provide a single-cell analysis. Immunohistochemistry (IHC) from bioptic material is informative, however it requires surgical intervention and does only provide a semi-quantitative read-out.

Thus, this invention relates to the use of preferred specific methods, such as a flow cytometry protocol for detection of hyper-acetylated histones, to be used in a variety of cellular samples, including blood/bone marrow samples.

This invention relates to the use of monoclonal antibodies termed T25 and T52 for the determination of histone acetylation levels in (tumor) samples to determine whether patients should be treated with HDACi and to follow the clinical outcome of such a treatment. The antibody can further be used to identify new HDAC inhibitors. Known HDAC inhibitors can be characterized in more detail. For example, a disorder which responds to the said HDAC inhibitor can be identified. The antibodies can further be used to evaluate advantageous dosages of certain HDAC inhibitors used to treat a disorder. The uses according to the invention may comprise steps (a) and (b) as described supra.

The invention further relates to the use of an antibody capable of binding to acetylated histone for determining whether a treatment of a disorder with an HDAC inhibitor is to be started/continued or not; and/or the classification of tumors. The preferred embodiments of the antibody to be used have been described supra.

Another aspect of the invention is an antibody capable of binding to a peptide having the sequence as shown in SEQ ID NO:4 but not to anyone of the peptides having the sequences as shown in SEQ ID NO:2, SEQ ID NO:6, SEQ ID NO:10 and SEQ ID NO:11. the antibody can be produced by per se known methods (Harlow and Lane, "Antibodies, A Laboratory Manual" CSH Press 1988, Cold Spring Harbor N.Y.).

The most preferred antibody termed T25 is produced by the hybridoma cell line termed G2M-T25-H4ac deposited at DSMZ.

Another antibody of the invention is the antibody termed T52 which is obtainable from the hybridoma cell line termed G2M-T52-ac deposited at DSMZ according to the provisions of the Budapest Treaty.

The invention further pertains to a hybridoma cell line producing an antibody according to the invention. The preferred hybridoma cell line is a hybridoma cell line which has the identifying characteristics of cell line G2M-T25-H4ac (being deposited at DSMZ). Another preferred hybridoma cell line is a hybridoma cell line which has the identifying characteristics of the cell line G2M-T52-ac (being deposited at DSMZ). The most preferred hybridoma cell lines produce one of the antibodies termed T25 and T52.

The invention also relates to a method for producing an antibody according to the invention comprising culturing hybridoma cells according to the invention under conditions which allow secretion of the antibody into the growth medium and obtaining the antibody from the medium. Methods for culturing the cells and obtaining antibodies from the medium are known in the art (Harlow and Lane, Antibodies, A Laboratory Manual" CSH Press 1988, Cold Spring Harbor N.Y.).

The invention is further directed to a diagnostic kit for determining the level of histone acetylation containing
(i) an antibody capable of binding to acetylated histone but not to deacetylated histone;
(ii) an HDAC inhibitor; and optionally
(iii) a secondary antibody directed against the antibody of step (i) and optionally
(iv) reagents for the measurement of a signal derived from an antibody binding to acetylated histones.

Examples of reagents referred to under (iv) above can be commonly used enzyme/substrate combinations for detection such as:
  a) Alkaline Phosphatase as enzyme together with the following substrates:
    1. 5-bromo-4-chloro-3-indolyl phosphate (BCIP) and nitroblue tetrazolium (NBT)
    2. naphtol-AS-MX-phosphate and fast red TR, or fast blue BN, or fast green (BN)
    3. Vector Red
    4. Vector Black
    5. Vectot Blue
    6. Horseradish Peroxidase as enzyme and 3,3-diaminobenzidine tetrahydrochloride (DAB) as substrate Other reagents used may be detected by immunofluorescence such as Fluorescein Isothiocyanate, Phycoerythrin, Green Fluorescent Protein, Red Fluorescent Protein, Yellow Fluorescent Protein, Texas Red, TRIC, Cy3, or Cy5. Other staining techniques can employ e.g. gold, rhodamine.

The preferred embodiments of the kit, in particular the preferred antibodies contained therein, correspond to the preferred embodiments of the method according to the invention.

In a further embodiment of the invention the antibodies T25 and/or T52 may be used to direct substances conjugated to these antibodies to sites of histone hyperacetylation in tissues where the hyperacetylation level is diagnostic of a diseased state. The antibodies T52 and/or T25 can be used in the manufacture of a medicament or diagnostic reagent for directing substances conjugated to these antibodies to sites of hyperacetylation. Such substances, may include, but are not limited to, radioactive compounds and chemotherapeutic or cytotoxic agents. At these sites, such conjugated substances may be released from the antibody by e.g., but not limited to, proteolytic cleavage. Examples of radioactive substances include but are not limited to alpha-particle emitting substances and gamma-emitting substances. Cytotoxic or chemotherapeutic agents are substances that inhibit the growth of cells or damage cells.

These substances are known to those skilled in the art and include calicheamicin, maytansinoids, $^{131}$iodine, $^{90}$yttrium, $^{186}$rhodium, $^{188}$rhodium, doxorubicin, daunorubicin, ricin A, Pseudomonas exotoxin, and others as reviewed in Paul Carter (Paul Carter, Improving the efficacy of antibody-based cancer therapies, Nature Reviews Cancer 2001; 1:118-129).

FIG. 1 shows the results of ELISA analyses testing the specificity of the antibodies T25 and T52 for acetylated histones (Example 1).

FIG. 2 shows a dose-dependent testing of the antibodies T25 and T52 by ELISA analysis (Example 1).

Figure 6:
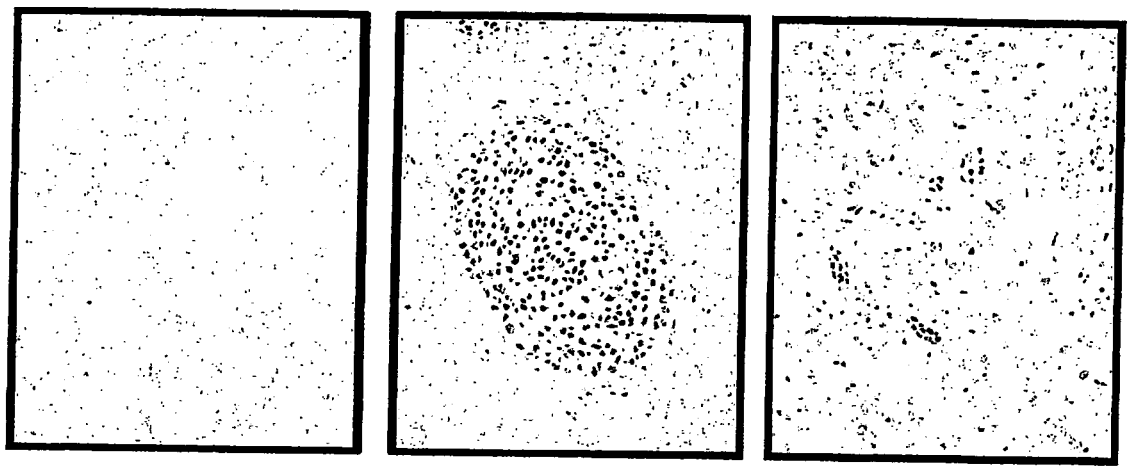

FIG. 6 displays a novel classification of human breast tumor cells according to their histone acetylation status (Example 2).

Figure 7:
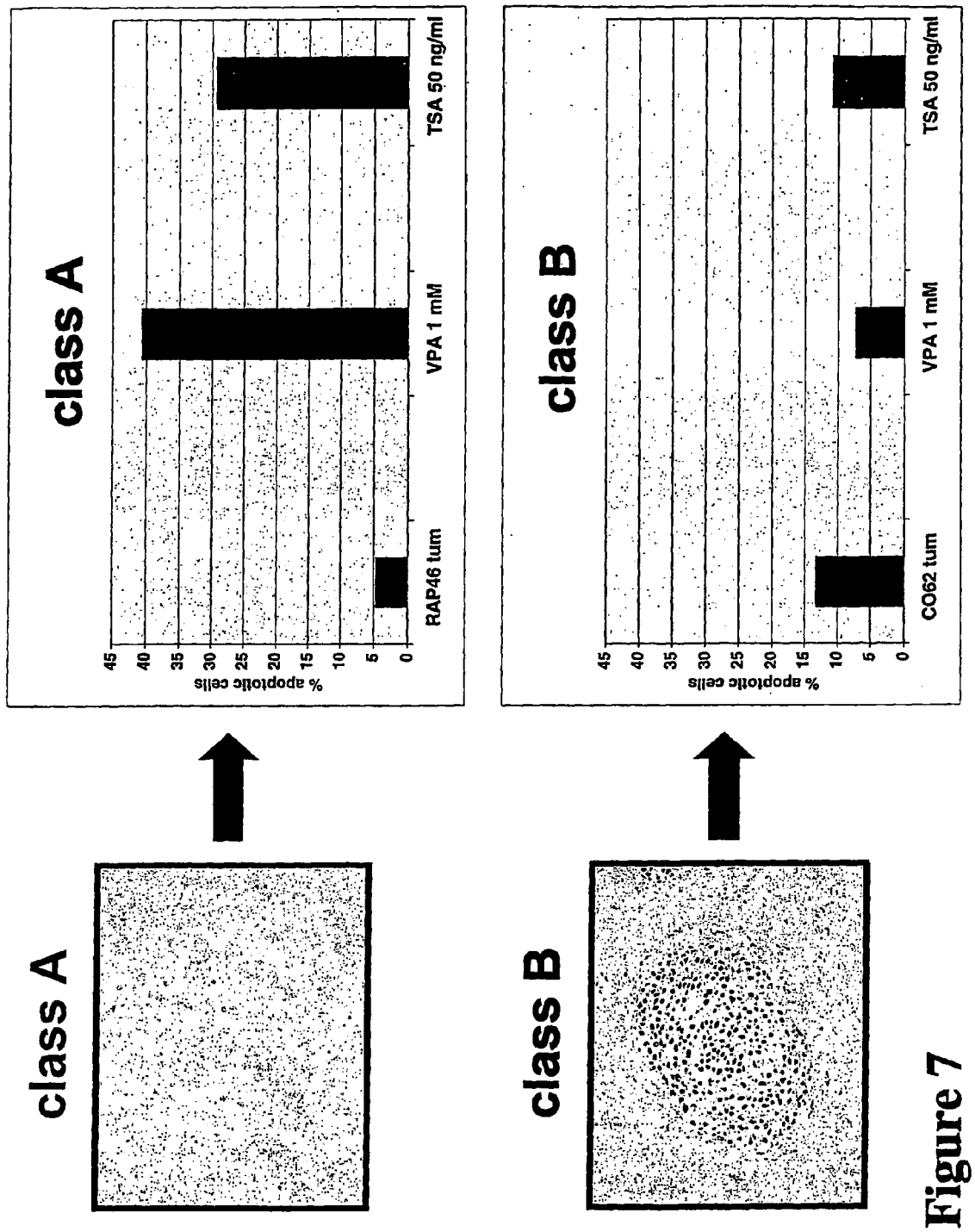

FIG. 7 shows the correlation between apoptosis induced by the HDACi and histone acetylation levels according to the classification presented in FIG. 6 of primary breast tumors (Example 2).

Figure 8:
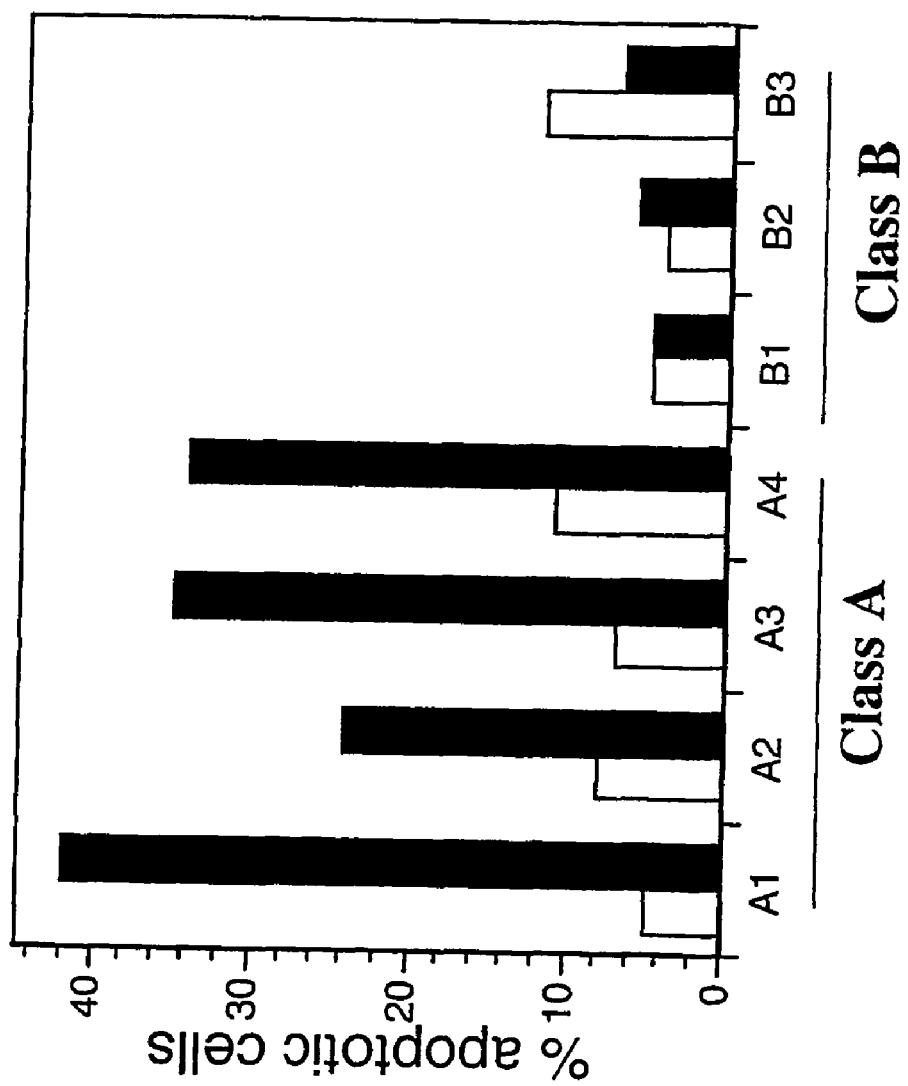

FIG. 8 shows the correlation between apoptosis induced by the HDACI and histone acetylation levels in additional cases of class "A" and "B" primary breast tumors (Example 2).

Figure 9:
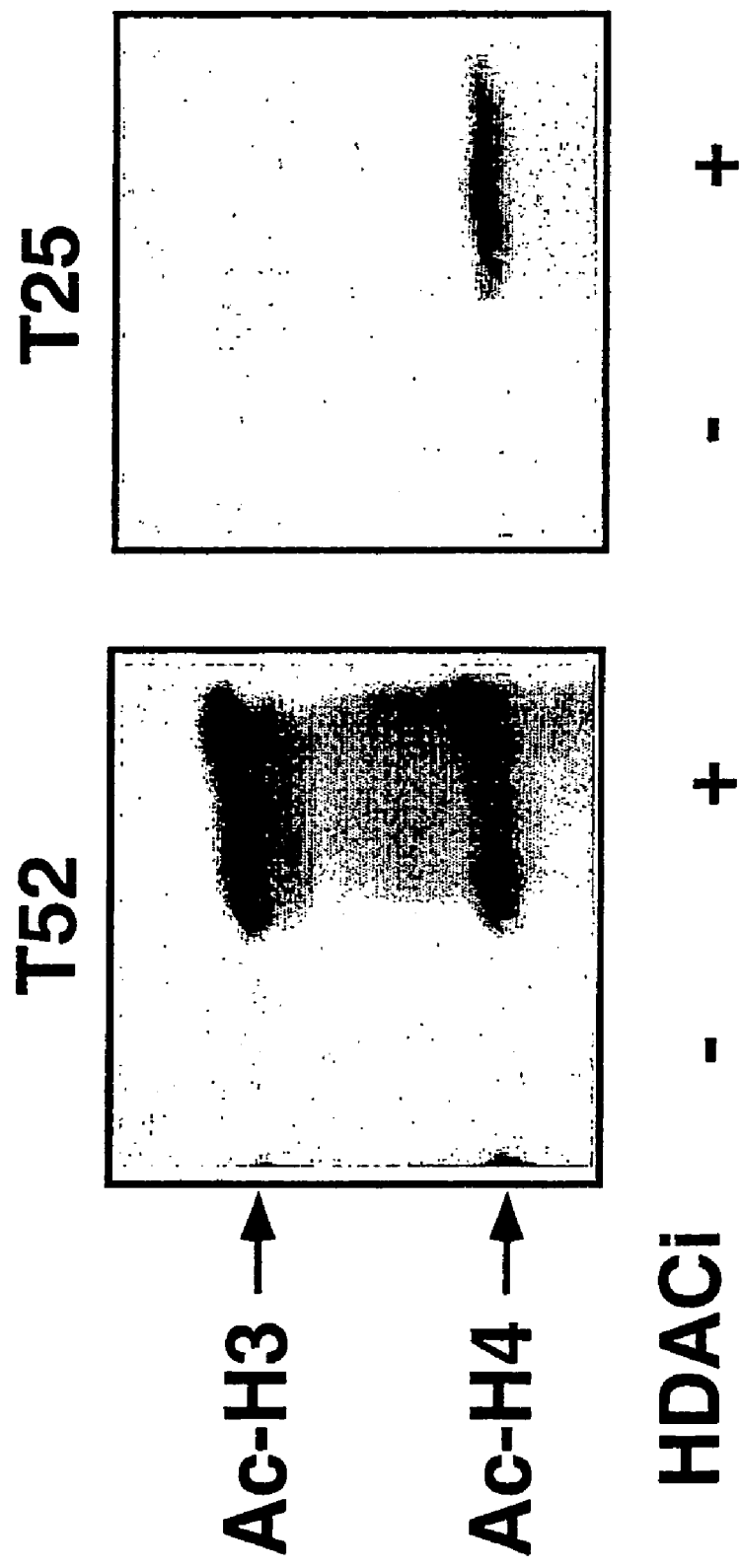

FIG. 9 displays in western blot analysis of U937 cells, either untreated or treated with the HDAC inhibitor TSA (Trichostatin A), that the T52 antibody recognizes acetylated histones H3 and H4 whereas the T25 antibody recognizes acetylated histone H4 only (Example 3).

Figure 10:
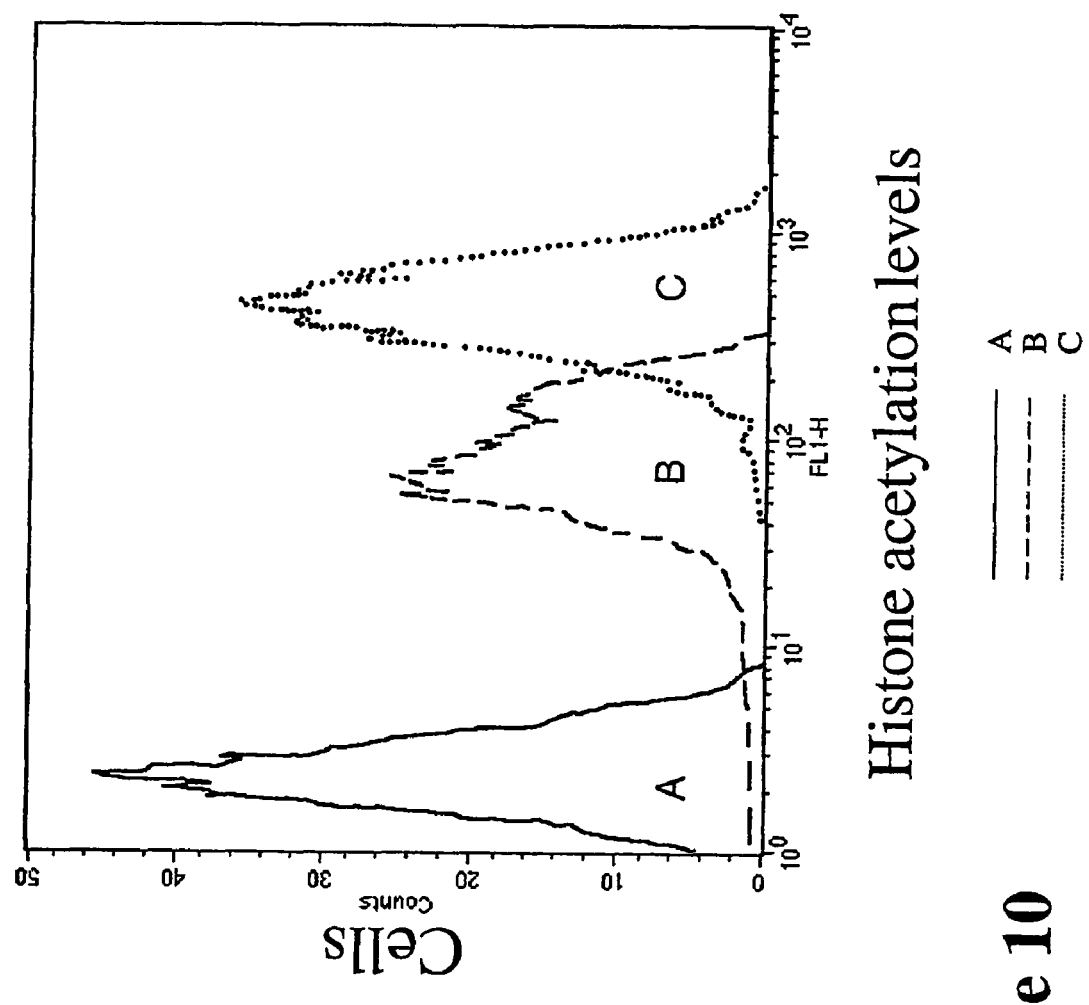

FIG. 10 shows the result of a flow cytometry analysis with U937 cells subjected to treatment with the HDAC inhibitor TSA using the antibody T52 (Example 3).

Figure 11:
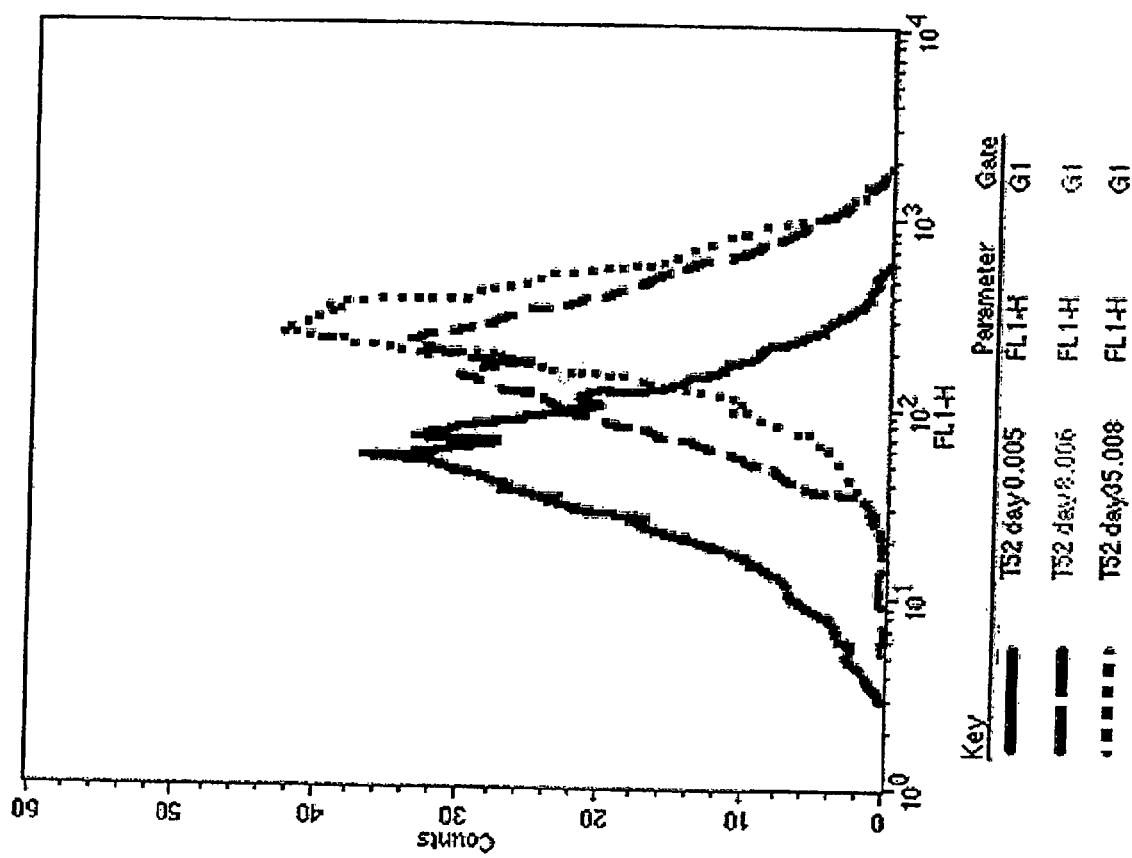

FIG. 11 shows the flow cytometry results measuring the cellular response to treatment with HDAC inhibitors in blood samples of patients (Example 3).

Figure 12:
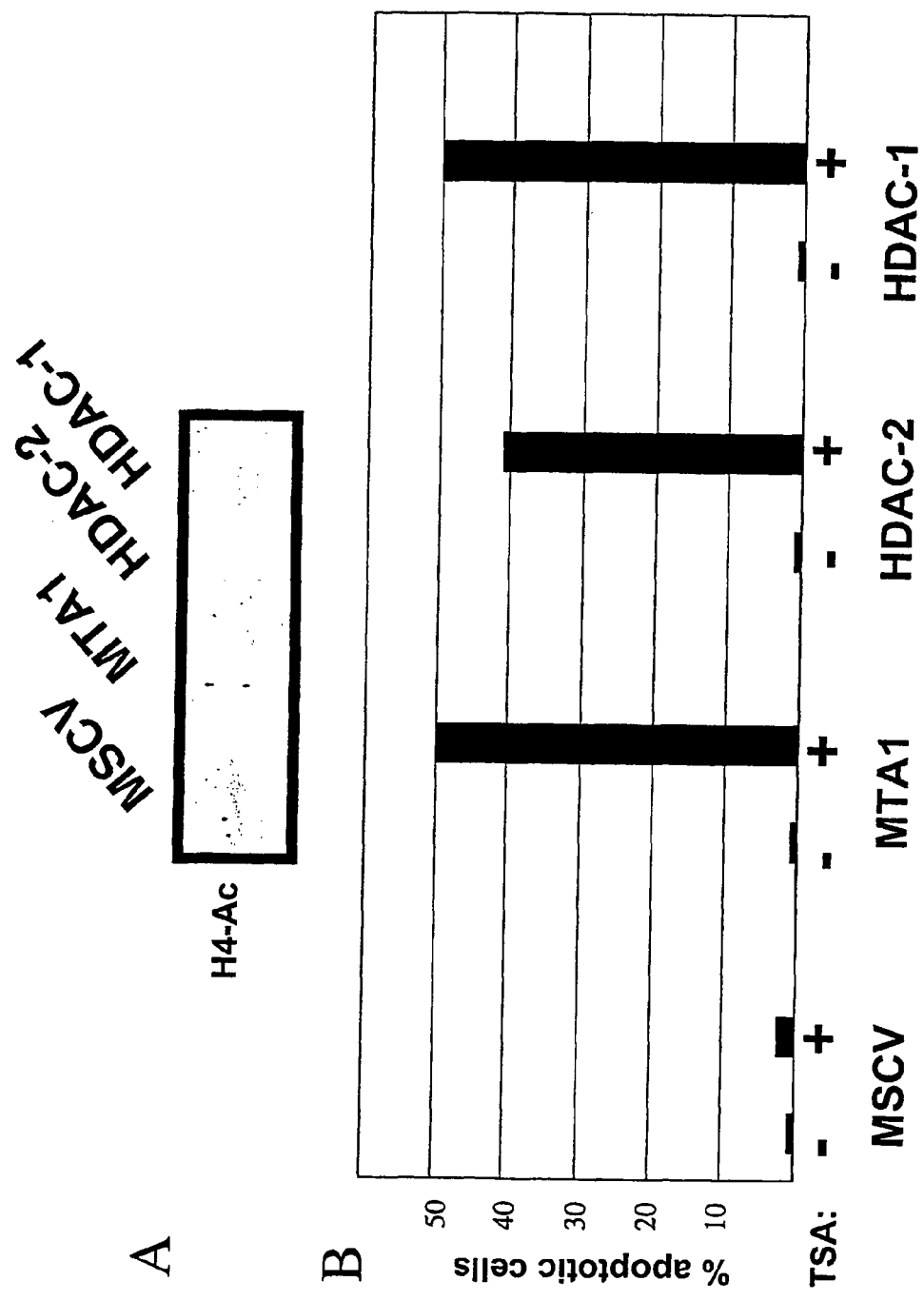

FIG. 12 shows the direct functional and therapeutically relevant correlation between levels of histone acetylation and sensitivity to HDAC inhibitors (Example 4).

The following examples further illustrate the invention:

EXAMPLE 1

Generation of monoclonal antibodies directed against acetylated histone H4, and acetylated lysine (FIGS. 1 and 2).

Method:

Mice were immunized with the peptide corresponding to the tetra-acetylated tail of histone H4 fused to KLH (sequence: KLH-SGRGK*GGK*GLGK*GGAK*R (SEQ ID NO: 1); 17amino acids, an asterisk indicates acetylated lysine). The underlined S-residue corresponds to amino acid no. 2 of the human histone H4 polypeptide sequence (see Swiss Prot P02304 for reference and therein). Mice were immunized following standard procedures (Antibodies: A Laboratory Manual. David Lane and Ed Harlow editors, Cold Spring Harbor Laboratory Press, 1990).

Hybridoma:
a) Spleen from Balb/c mouse;
b) Myeloma used for fusion:
  SP2/0 Ag14 purchased from ECACC ref. No. 85072401.

The screening of the monoclonal antibodies was performed by ELISA, using the following biotinylated peptides:

| | |
|---|---|
| SGRGK*GGK*GLGK*GGAK*R | (SEQ ID NO: 1; immunogen, tetra-acetylated histone H4 tail); |
| SGRGKGGKGLGKGGAKR | (SEQ ID NO: 2; non acetylated peptide, to screen for antibodies able to recognize the histone tail irrespective of acetylation state); |
| SGRGK*GGKGLGKGGAKR | (SEQ ID NO: 3; histone H4 tail, mono-acetylated at lysine 5); |
| SGRGKGGK*GLGKGGAKR | (SEQ ID NO: 4; histone H4 tail, mono-acetylated at lysine 8); |
| SGRGKGGKGLGK*GGAKR | (SEQ ID NO: 5; histone H4 tail, mono-acetylated at lysine 12); |
| SGRGKGGKGLGKGGAK*R | (SEQ ID NO: 6; histone H4 tail, mono-acetylated at lysine 16); |
| SGRGK*GGKGLGK*GGAKR | (SEQ ID NO: 7; histone H4 tail, di-acetylated at lysines 5, 12); |
| SGRGKGGK*GLGKGGAK*R | (SEQ ID NO: 8; histone H4 tail, di-acetylated at lysines 8,16); |
| SGRGKGGK*GLGK*GGAK*R | (SEQ ID NO: 9; histone H4 tail, tri-acetylated at lysines 8, 12, 16); |
| SGRGK*GGK*GLGK*GGAK*R | (SEQ ID NO: 1; histone H4 tail, tetra-acetylated at lysines 5, 8, 12, 16); |
| AVCDK*CLK*FYSK* | (SEQ ID NO: 10; 12aa, 3 Ac-K); |
| VWDQEFLK*VDQG | (SEQ ID NO: 11; 12aa, 1 Ac-K); |

The last two peptides were used to check whether the antibodies were able to recognize acetylated lysine in contexts different from the histone H4 tail.

Results:

The results are presented in FIGS. 1 and 2 where the specificities of the antibodies T25 and T52 are analysed in ELISA tests using a set of acetylated and non-acetylated peptides.

ELISA Protocol:
  50 µl/well of a solution 5 µg/ml streptavidin in 50 mM carbonate buffer, pH9 were incubated overnight at 4° C.;
  200 µl/well BSA 3% was applied for 1 h at 37° C.;
  50 µl/well acetylated biotinylated peptides (2 µg/ml in PBST) were applied for 1 h at 37° C.;
  50 µl/well of the various antibodies (either as supernatant from the hybridoma plates, or as purified antibodies at the indicated concentrations) in PBST+BSA (1 mg/ml) were applied for 2 h at 37° C.;
  6 washes in PBST (10 minutes each)
  Detection of bound monoclonal antibodies with 50 µl/well of an anti-mouse antibody conjugated with HRP (horse redish peroxidase) 1:5000 in PBST, BSA 1 mg/ml for 30 min at 37° C.

The monoclonal antibodies T25 and T52 were selected on the basis of their recognition of acetylated Histone H4 derived peptides and their specificities tested further by ELISA. The resulting data are presented in FIGS. 1-2 and can be summarized as follows:

Clone T25:

Specificity:
  Histone H4 acetylated at lysine 8: +++
  Histone H4 acetylated at lysine 12: +

Not reactive:
  Histone H4 acetylated at lysine 5 or 16
  Unrelated peptides acetylated on lysine
  Non acetylated histone H4

Clone T52:

Specificity:
  Acetylated lysine in any context

Not Reactive:
  Non-acetylated peptides

In additon a dose-dependent testing of the antibodies T25 and T52 has been performed also by ELISA analysis. The antibodies were tested at two different concentrations to evaluate their dose-dependent variation in signal intensity (FIG. 2).

The hybridoma cell lines producing T25 and T52, respectively, have been deposited on Sep. 24, 2002 with the DSMZ (Deutsche Sammlung von Mikroorganismen und Zelikulturen, Mascheroder Weg 1b, D-38124 Braunschweig, Germany; German Collection of Microorganisms and Cell Cultures) in accordance with the provisions of the Budapest Treaty.

The hybridoma cell line having the identification reference G2M-T25-H4ac produces the antibody T25. The hybridoma cell line having the identification reference G2M-T25-H4ac has been given the accession number ACC2578. The hybridoma cell line having the identification reference G2M-T52-ac produces the antibody T52. The hybridoma cell line having the identification reference G2M-T52-ac has been given the accession number ACC2579.

The hybridoma cell lines can be cultured under conditions known to those skilled in the art. Culture medium and conditions may be as follows:

| HT: for 500 ml | |
|---|---|
| ISCOVE Mod. Dulbecco Medium base | 418 ml |
| FBS | 50 ml |
| Pen/strep (100×) | 5 ml |
| HT (hypoxanthine, thymidine) (50×) | 10 ml |
| Sodium Pyruvate (100 mM) | 6 ml |
| Non essential Aminoacids (100×) | 6 ml |
| Glutamine (100×) | 5 ml |
| $CO_2$: 5%/37° C. | |

BM-Condimed H1 Hybridoma growing supplement (Roche) may be added at 10% for the first week of culture, then reduced to 5%.

The cells may be split 1:2/1:3 every two days.

EXAMPLE 2

The use of the monoclonal antibody T25 (directed against acetylated histone H4) in immunohistochemistry, to measure histone H4 acetylation levels in patient samples, and to predict the clinical response to treatment with inhibitors of histone deacetylases (HDACi) (FIGS. 3-8).

The studies so far performed on the modulation of chromatin structure and function by histone acetylation have been focused on mechanistical aspects, and—in mammals—almost exclusively conducted in established model systems based on immortalized/transformed cell lines. Although these studies have been extremely informative, and have provided crucial insights, the precise role of histone acetylation (at the global level, and at specific genomic areas) in physiological situations is not well characterized: this lack of knowledge does currently not allow to formulate specific mechanistical hypotheses on the alterations of such phenomenon in pathological situations. It is clear, however, that alterations in the functioning of histone modifiers may play a critical role in the pathogenesis of several diseases, including cancer (Brown and Strathdee, 2002, Trends Mol Med 8, S43-8; Chinnadurai, 2002, Mol Cell 9, 213-24; Robertson, 2002, Oncogene 21, 5361-79). HDAC inhibitors (HDACi) have been shown to behave as anti-proliferative, pro-apoptotic and pro-differentiative agents with high selectivity for tumor cells versus normal cells, although the mechanism behind this selectivity are not known (Marks et al., 2001, Nat Rev Cancer 1, 194-202). Furthermore, the finding that overexpression of a NAD-dependent histone deacetylase in yeast and *C. elegans* (SIR2) leads to extended life-span indicates that regulation of histone acetylation may be critical for timing cell and organismal aging (Tissenbaum and Guarente, 2001, Nature 410, 227-30).

Method:

The monoclonal antibodies developed and described above (see Example 1) were used to perform immunohistochemical studies of histone H4 aectylation levels in various physiological/pathological situations. Here, the antibody T25, that selectively recognizes the acetylated histone H4 was used. This antibody does not cross-react with other histones, and does not recognize non histone proteins.

Results:

To evaluate the specificity of the T25 antibody in immunohistochemistry (IHC), the inventors performed a preliminary test in an established cell line (U937 cells). These cells grow in suspension, and after treatment in vitro with HDACI (such as trichostatin A or VPA for 6-12 hours) they show a drastic increase in the levels of acetylated histone H3 and histone H4 by Western blot (FIG. 3A). Untreated cells, or cells treated for 12 hours with VPA (1 mM), were either processed for Western blot analysis (FIG. 3A), or fixed in formalin and then processed for immunohistochemistry (FIG. 1B). The increase in the levels of acetylated histone H4 observed in Western blot of FIG. 1A was paralleled perfectly by the increase in the intensity of staining and number of stained cell nuclei observed in immunohistochemistry (FIG. 3B). The T25 antibody can therefore be used for the analysis of histone acetylation levels by western blot analysis and immunohistochemistry (IHC).

Figure 3:
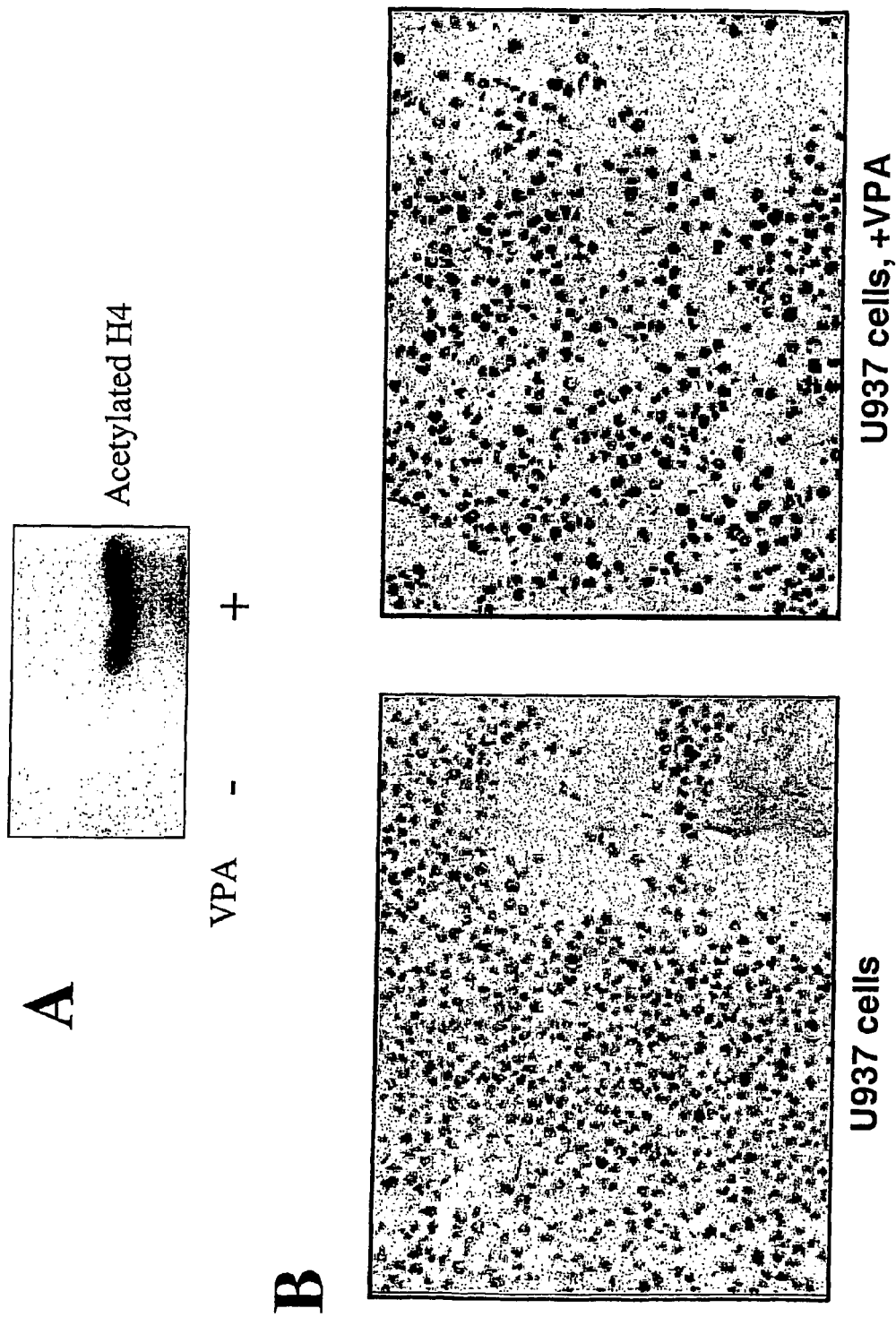
FIG. 3 shows the specificity of the T25 antibody in western blots and immunohistochemistry (IHC) using an established cell line (U937 cells) (Example 2).
Figure 4:
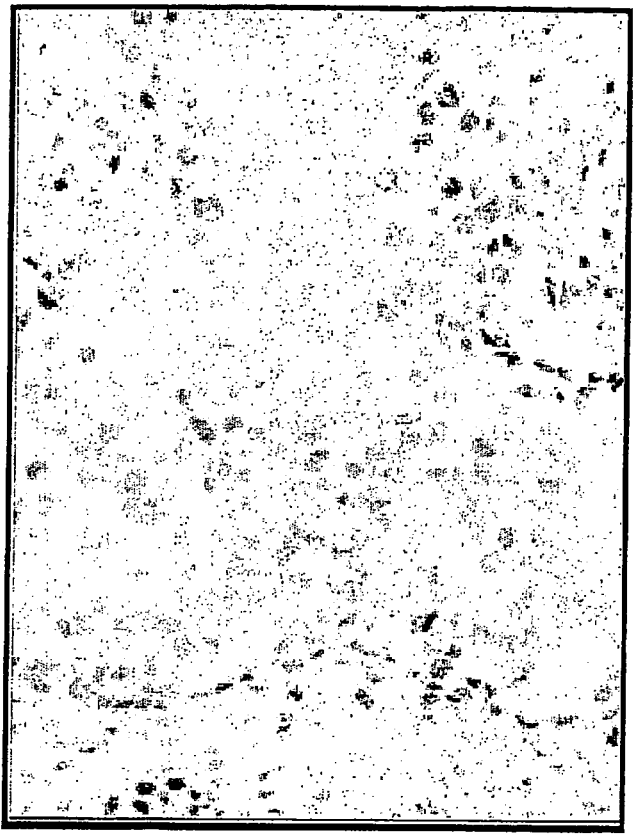
FIG. 4 shows an analysis by immunohistochemistry (IHC) on human breast tissue using the T25 antibody, revealing alterations in human breast tumor tissue histone acetylation levels compared to normal tissues (Example 2).
Figure 4:
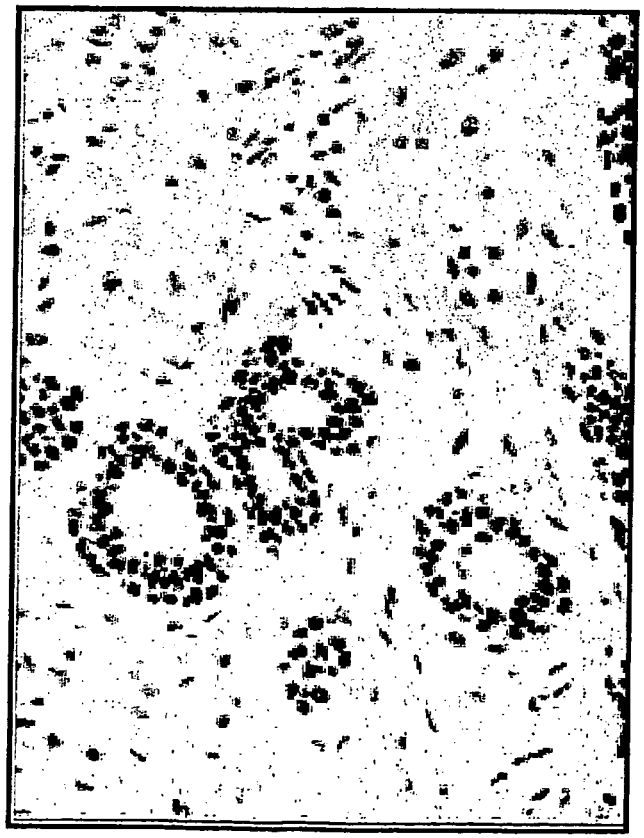
Figure 5:
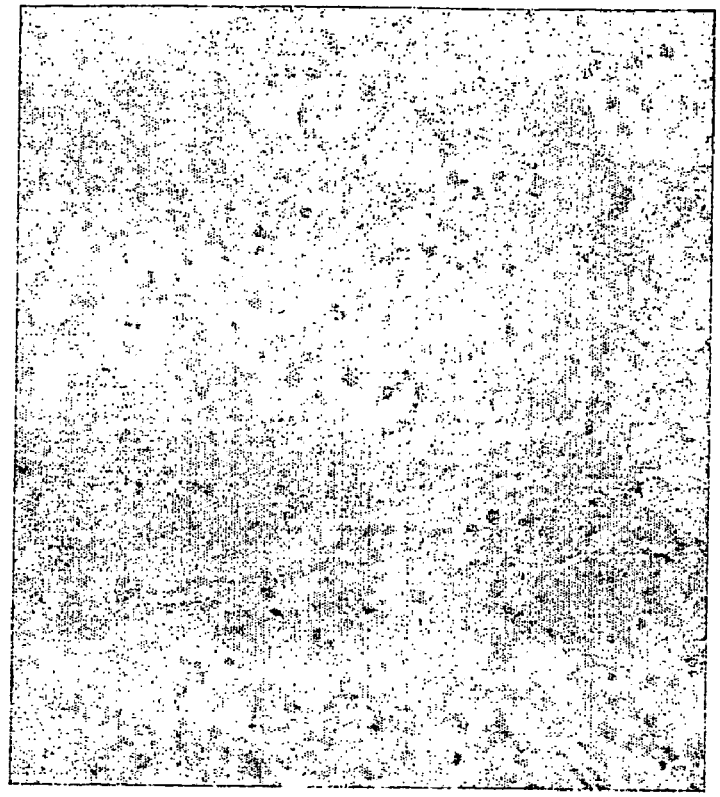
FIG. 5 shows an analysis by immunohistochemistry (IHC) of human colon tissue using the T25 antibody revealing alterations in human colon tumor tissue histone acetylation levels compared to normal tissues (Example 2).
Figure 5:

Furthermore, IHC analysis of tumor samples revealed in several cases an alteration in histone acetylation levels compared to normal tissues. In FIG. 4, an example from human breast tissues is shown: compared to normal breast tissue (left panel), where the nuclei of the ductal cells are intensely stained with the T25 antibody, tumor cells (right panel) are uniformly negative for T25 staining, revealing a globally hypoacetylated state. This finding is not restricted to breast tissues: in FIG. 5, a similar result is shown for a colon cancer case.

The further evaluation of more than 50 breast tumor samples revealed a novel classification of tumor samples according to their acetylation levels of histone H4. Of these samples analysed, 51% were classified as "class A" (i.e. globally hypoacetylated); 31% as "class B" (i.e. normal to high levels of histone acetylation); 18% as "class C" (i.e. heterogeneous pattern of histone acetylation) (FIG. 6). It appears therefore that human tumors can be classified on the basis of their level of histone H4 acetylation level, and that this method may be used to classify tumors (based on immunohistochemical staining with the T25 antibody, in comparison to normal tissue) on the basis of their histone H4 acetylation patterns.

To establish whether this classification may have additional correlations with tumor biology and potential influences on the choice of clinical therapeutic treatments, the sensitivity of tumor cells derived from "class A" or "class B" primary human breast tumors to various HDAC inhibitors was evaluated in vitro (FIG. 7-8). To investigate this further, cells derived from excision surgery of primary breast tumors were cultured (on which in parallel IHC using the T25 antibody was performed to establish the histone acetylation levels in vivo) following standard procedures (Elenbaas et al., 2001, Genes Dev 15, 50-65). After a few passages in culture (in the absence of fetal bovine serum, to eliminate contamination of fibroblasts), the cell population is greatly enriched in tumor cells. The bulk populations of cells derived from four "class A" and three "class B" tumors were then treated with VPA, or TSA (FIGS. 7-8). As shown in FIGS. 7-8, a dramatic correlation between apoptosis induced by the HDAC inhibitors and histone acetylation levels of the primary tumor was observed: in fact, only the cells derived from "class A" tumors (i.e. globally hypoacetylated) showed apoptosis upon treatment with the HDAC inhibitors, whereas cells from "class B" tumors were totally resistant. The immunohistochemical classification as described here, can therefore be used to predict the response of tumor cells to treatment with HDAC inhibitors and could thus be used for prognostic predictions whether a patient should be treated with such inhibitors.

EXAMPLE 3

On the use of the monoclonal antibody T52 (directed against aceteylated lysine) in cytofluorimetry to determine (i) the acetylation levels in patient samples and (ii) the cellular response to treatment with HDAC inhibitors (FIGS. 9-11).

The monoclonal antibody T52 recognizes acetylated lysine in several contexts (see also FIGS. 1-2). Western blot analysis of U937 cells, either untreated or treated with the HDAC inhibitor TSA, showed that the only detectable bands using the T52 antibody corresponded to acetylated histones H3 and H4 which were greatly increased upon treatment with the HDACi (FIG. 9). For comparison, western blot using the T25 antibody (that recognizes acetylated histone H4 only) only showed the histone H4 band (FIGS. 3A and 9).

Method:

Human U-937 cells were grown in RPMI-1640 medium supplemented with 10% Fetal Bovine Serum in standard culture conditions.

Exponentially growing U-937 cells were treated for 4 hrs with 10 ng/ml Trichostatin A (TSA, Sigma Aldrich). After the treatment cells were washed with cold phosphate buffer saline (PBS), counted and fixed in 1% formaldehyde in PBS for 15 minutes. Fixed cells were then washed, resuspended in PBS, and stocked at 4° C.

Histone acetylation analysis was performed according to the following procedure. Cells were fixed for 15 minutes in 1% formaldehyde in PBS. $1 \times 10^6$ cells/sample were washed with PBS+1% BSA and permeabilised with 200 µl of 0.1%

Triton X100 in PBS for 10 min at room temperature (to allow for the antibody to reach acetylated nuclear proteins, such as histones). After washing with PBS+1% BSA pellets were incubated with 500 µl of 10% normal goat serum (NGS) in PBS for 20 min at 4° C. Histone acetylation levels were detected by incubation with T52 mouse monoclonal antibody (1 µg/ml in PBS+1% BSA). Detection was performed by incubation with a fluorescein isothiocyanate (FITC)-conjugated affinity pure F(ab')2 fragment of goat anti-mouse IgG (Sigma) for 1 h at room temperature in the dark.

Flow cytometry analysis was performed using a FACScan flow cytometer (Becton Dickinson), acquiring at least 10,000 events/sample. The instrument was equipped with a bandpass 530/30 nm optical filter for FITC fluorescence detection (FL1 channel) and a 650 nm longpass optical filter in front of the PI (FL3) channel detector. Cells doublets were discriminated by pulsed processor analysis according to the comparison of peak and area electronic signals from the FL3.

Results:

Exponentially growing U937 cells were subjected to treatment with TSA. T52 staining evidenced an increase in the mean fluorescence (FL1-H) of TSA treated in comparison to non-treated exponentially growing cells, indicating an increase in histone acetylation levels. The mean fluorescence value for untreated U937 exponentially growing cells was 90 (FIG. 10, curve B). The mean fluorescence value for U937 cells treated with 10 ng/ml TSA for 4 hrs was 450 (FIG. 10, curve C). Control blank staining showed an expected relevant baseline signal from acetylated histones under these growth conditions (curve A; mean fluorescence value: 3).

Due to the large amount of HDAC proteins present in the cells, deacetylation activity is very high. Consequently the pre-fixation steps became very important for maintaining histones in an hyperacetylated state and avoiding artifacts. All the washings were performed in a refrigerated centrifuge using cold PBS, while cells were finally fixed on ice. Removal of cell culture medium containing TSA and substitution with PBS can cause complete loss of the enhanced acetylation signal, even during the few minutes needed for the pre-fixation washings. Ethanol fixation is not compatible with acetylated histone detection, consequently a first incubation with 1% formaldehyde was needed if alcoholic treatment was subsequently used for DNA staining in cell cycle analysis.

The data obtained in U937 cells demonstrated the validity of the flow cytometry approach, and the possibility to measure the cellular response to HDAC inhibitors.

HDAC inhibitors are currently being tested for their clinical use in tumor patients (Marks et al., 2001, Nat Rev Cancer 1, 194-202). Therefore, the inventors evaluated the response to valproic acid, VPA (a HDAC inhibitor currently in clinical trials for several forms of cancer), in blood samples of patients subjected to VPA treatment. An example is shown in FIG. 11. Peripheral blood was collected periodically before/ at various times of VPA treatment (10 to 30 mg/kg/day; plasmatic VPA concentration: 0,75 mM), mononuclear cells were isolated by Ficoll analysis and then analyzed as described. Histone acetylation levels increased >3 fold after 7-days of VPA treatment (day 8), and further increased at day 28-35 (FIG. 11). These results show the feasibility of measuring histone acetylation levels by flow cytometry of blood samples from patients affected by any kind of tumors. The histone acetylation level measured in blood cells may serve as marker to evaluate the efficacy of HDAC inhibitor treatment of patients suffering from tumors, including solid tumors, to further orientate the treatment schedule.

EXAMPLE 4

Method:

To demonstrate that changes in histone acetylation levels are directly functionally and therapeutically relevant linked to the phenomenon of sensitivity to HDAC inhibitors, a primary tumor-derived cell culture, characterized by high levels of histone acetylation, was transduced with retroviral expression constructs for HDAC-1, HDAC-2, or MTA1 (or control=MCSV). Two days after transduction, the treatment with various HDAC inhibitors was started (TSA is shown in FIG. 12). An aliquot of the cells was collected, and Western blot analysis (using antibodies directed against acetylated histone H4) was performed on protein extracts prepared from these cells, to verify that overexpression of either HDAC, or of MTA1, led to a decrease in histone acetylation levels of the tumor cells.

Results:

As can be seen in FIG. 12A, the control-transduced cells displayed detectable levels of histone H4 acetylation (detected using the T25 antibody) and were resistant to TSA treatment (FIG. 12B), whereas all of the tumor cells transduced with HDAC/MTA constructs displayed histone hypoacetylation (FIG. 12A), due to the additionally introduced HDAC activity. Accordingly these cells became highly sensitive (up to 50% apoptosis) to HDAC inhibitor treatment (FIG. 12B).

These data clearly demonstrate that there is a direct correlation between levels of histone H4 acetylation and the sensitivity to HDAC inhibitor treatment. This verifies functionally and therapeutically relevant the use of antibodies, such as T25, detecting histone H4 acetylation levels in tumor cells as a method to select for responsiveness to therapies based on inhibition of HDAC activity.

We claim:

1. A method for the diagnosis of or the prognosis of a treatment for a disorder with an HDAC inhibitor comprising
   (a) contacting a sample obtained from a tissue affected by the disorder with a monoclonal antibody which is
   (1) monoclonal antibody T25 which is obtainable from the cell line G2M-T25-H4ac deposited at DSMZ (accession no. ACC2578); or
   (2) monoclonal antibody T52 which is obtainable from the cell line G2M-T52-ac deposited at DSMZ (accession no. ACC2579);
   wherein each of said T25 or T52 monoclonal antibody is capable of binding to acetylated histone but not to deacetylated histone; and
   (b) determining the level of histone acetylation in the sample with said T25 or said T52 antibody;
   wherein lowered level of histone acetylation in said sample compared to that of a reference sample is indicative that said disorder is treatable with said HDAC inhibitor.

2. A method according to claim 1 wherein the antibody is the antibody T25 which is obtainable from the cell line G2M-T25-H4ac deposited at DSMZ (accession no. ACC2578).

3. A method according to claim 1 wherein the antibody is the antibody T52 which is obtainable from the cell line G2M-T52-ac deposited at DSMZ (accession no. ACC2579).

4. A method according to claim 1 wherein the disorder is
   a tumor disease wherein induction of hyperacetylation of histones has a beneficial effect resulting in differentiation and/or apoptosis of a patient's tumor cells,
   a disease that show aberrant recruitment of HDAC activity,
   a condition associated with abnormal gene expression,
   an autoimmune disease, or
   a proliferative disease.

5. A method according to claim 4 wherein the disorder is, melanoma, estrogen receptor-dependent and independent breast cancer, ovarian cancer, testosterone receptor-dependent and independent prostate cancer, colon and colorectal cancer, stomach cancer, head and neck cancer, small cell and non-small cell lung carcinoma, leukemia, lymphomas or thyroid resistance syndrome.

6. A method according to claim 1 wherein in step (b) the level of histone acetylation in the sample is determined by flow cytometry, immunohistochemistry, ELISA or Western Blotting.

7. A method according to claim 1 wherein the reference sample is a sample obtained from a tissue from a healthy individual that corresponds to the tissue affected by the disorder and said method comprises processing the reference sample according to steps (a) and (b).

8. A method according to claim 1 wherein the reference sample is a sample obtained from tissue affected by the disorder which has been contacted with an HDAC inhibitor and said method comprises processing the reference sample according to steps (a) and (b).

9. A method for the classification of a tumor comprising
   (a) contacting a sample obtained from a tissue affected by the tumor with a monoclonal antibody which is
   (1) monoclonal antibody T25 which is obtainable from the cell line G2M-T25-H4ac deposited at DSMZ (accession no. ACC2578);
   (2) monoclonal antibody T52 which is obtainable from the cell line G2M-T52-ac deposited at DSMZ (accession no. ACC2579); or
   (3) a conjugate of (1) or (2);
   wherein each of said T25 or T52 monoclonal antibody is capable of binding to acetylated histonebut not to deacetylated histone; and
   (b) determining the level of histone acetylation in the sample with said T25 or said T52 antibody;
   wherein lowered level of histone acetylation in said sample compared to that of a reference sample is indicative that said tumor is treatable with an HDAC inhibitor.

10. The method according to claim 9 wherein the conjugate comprises a radioactive compound.

11. The method according to claim 9 wherein the conjugate comprises a chemotherapeutic or cytotoxic agent.

12. The method according to claim 9 wherein the conjugate is released by proteolytic cleavage.

* * * * *

SEQUENCE LISTING

<160> NUMBER OF SEQ ID NOS: 11

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)

```
<223> OTHER INFORMATION: Acetylation
<220> FEATURE:
<221> NAME/KEY: MOD_RES
<222> LOCATION: (8)..(8)
<223> OTHER INFORMATION: Acetylation
<220> FEATURE:
<221> NAME/KEY: MOD_RES
<222> LOCATION: (12)..(12)
<223> OTHER INFORMATION: Acetylation
<220> FEATURE:
<221> NAME/KEY: MOD_RES
<222> LOCATION: (16)..(16)
<223> OTHER INFORMATION: Acetylation

<400> SEQUENCE: 1

Ser Gly Arg Gly Lys Gly Gly Lys Gly Leu Gly Lys Gly Gly Ala Lys
1               5                   10                  15
Arg

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Gly Arg Gly Lys Gly Gly Lys Gly Leu Gly Lys Gly Gly Ala Lys
1               5                   10                  15
Arg

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acetylation

<400> SEQUENCE: 3

Ser Gly Arg Gly Lys Gly Gly Lys Gly Leu Gly Lys Gly Gly Ala Lys
1               5                   10                  15
Arg

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Acetylation

<400> SEQUENCE: 4

Ser Gly Arg Gly Lys Gly Gly Lys Gly Leu Gly Lys Gly Gly Ala Lys
1               5                   10                  15
Arg

<210> SEQ ID NO 5
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Acetylation

<400> SEQUENCE: 5

Ser Gly Arg Gly Lys Gly Gly Lys Gly Leu Gly Lys Gly Gly Ala Lys
1               5                   10                  15

Arg

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Acetylation

<400> SEQUENCE: 6

Ser Gly Arg Gly Lys Gly Gly Lys Gly Leu Gly Lys Gly Gly Ala Lys
1               5                   10                  15

Arg

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acetylation
<220> FEATURE:
<221> NAME/KEY: MOD_RES
<222> LOCATION: (12)..(12)
<223> OTHER INFORMATION: Acetylation

<400> SEQUENCE: 7

Ser Gly Arg Gly Lys Gly Gly Lys Gly Leu Gly Lys Gly Gly Ala Lys
1               5                   10                  15

Arg

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Acetylation
<220> FEATURE:
<221> NAME/KEY: MOD_RES
<222> LOCATION: (16)..(16)
<223> OTHER INFORMATION: Acetylation
```

```
<400> SEQUENCE: 8

Ser Gly Arg Gly Lys Gly Gly Lys Gly Leu Gly Lys Gly Gly Ala Lys
1               5                   10                  15

Arg

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Acetylation
<220> FEATURE:
<221> NAME/KEY: MOD_RES
<222> LOCATION: (12)..(12)
<223> OTHER INFORMATION: Acetylation
<220> FEATURE:
<221> NAME/KEY: MOD_RES
<222> LOCATION: (16)..(16)
<223> OTHER INFORMATION: Acetylation

<400> SEQUENCE: 9

Ser Gly Arg Gly Lys Gly Gly Lys Gly Leu Gly Lys Gly Gly Ala Lys
1               5                   10                  15

Arg

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acetylation
<220> FEATURE:
<221> NAME/KEY: MOD_RES
<222> LOCATION: (8)..(8)
<223> OTHER INFORMATION: Acetylation
<220> FEATURE:
<221> NAME/KEY: MOD_RES
<222> LOCATION: (12)..(12)
<223> OTHER INFORMATION: Acetylation

<400> SEQUENCE: 10

Ala Val Cys Asp Lys Cys Leu Lys Phe Tyr Ser Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Acetylation

<400> SEQUENCE: 11

Val Trp Asp Gln Glu Phe Leu Lys Val Asp Gln Gly
1               5                   10
```